United States Patent
Lee et al.

(10) Patent No.: US 8,149,413 B2
(45) Date of Patent: Apr. 3, 2012

(54) SURFACE PLASMON RESONANCE SENSING DEVICE

(75) Inventors: Chung-Pei Lee, Taipei (TW); Yu-Chia Tsao, Taipei (TW); Woo-Hu Tsai, Taipei (TW); Hsiang-Chih Hsu, Taipei (TW)

(73) Assignee: Forward Electronics Co., Ltd. (TW)

( * ) Notice: Subject to any disclaimer, the term of this patent is extended or adjusted under 35 U.S.C. 154(b) by 100 days.

(21) Appl. No.: 12/662,545

(22) Filed: Apr. 22, 2010

(65) Prior Publication Data

US 2011/0157590 A1    Jun. 30, 2011

(30) Foreign Application Priority Data

Dec. 31, 2009   (TW) ................................ 98146314 A (51) Int. Cl.
*G01N 21/55* (2006.01)

(52) U.S. Cl. ........................................ 356/445; 356/317

(58) Field of Classification Search .......... 356/445–448, 356/317–318; 436/515–516; 250/306–307; 422/82.05–82.11; 435/808

See application file for complete search history.

(56) References Cited

U.S. PATENT DOCUMENTS

| 6,139,797 A * | 10/2000 | Suzuki et al. ............... 422/82.05 |
| 2010/0171958 A1 * | 7/2010 | Chau et al. .................... 356/445 |
| 2011/0157593 A1 * | 6/2011 | Miyadera et al. ............. 356/445 |

* cited by examiner

*Primary Examiner* — Tri T Ton
(74) *Attorney, Agent, or Firm* — Bacon & Thomas, PLLC (57) ABSTRACT

A surface plasmon resonance sensing device that is portable, and having the fiber sensing unit whose resonant wavelength being within the transmission range of a single-mode fiber or a multi-mode fiber, is disclosed. The disclosed sensing device comprises: a light source unit, a fiber sensing unit, an optical sensor, a plurality of fibers, and a computing and displaying unit. The fiber sensing unit includes a trench, a cladding layer, a core layer, a first metallic layer, and a plurality of dielectric thin film layers, wherein the first metallic layer covers the trench, and the plurality of dielectric thin film layers forms on the first metallic layer. The light source provided by the light source unit will become a light signal, after the light passes through the fiber sensing unit. The optical sensor transforms the light signal into a corresponding electric signal, for the usage of the computing and displaying unit.

19 Claims, 6 Drawing Sheets

SURFACE PLASMON RESONANCE SENSING DEVICE

BACKGROUND OF THE INVENTION

1. Field of the Invention

The present invention relates to a surface plasmon resonance sensing device and, more particularly, to a surface plasmon resonance sensing device which is portable, and the resonant wavelength of the fiber sensing unit thereof being within the transmission range of a single-mode fiber or the transmission range of a multi-mode fiber.

2. Description of Related Art

For applications in medical and environmental detection, it is essential to identify the species and concentrations of the biomolecules rapidly and accurately. For example, in environmentally hazardous occasions, the responding staff must first identify the species and the concentrations of the harmful materials at the site, so as to decide the subsequent procedures of treatment according to the detection results and minimize the risks of the treatment. Thus, accuracy, sensitivity, simplicity in operation procedures and portability are important.

To date, surface plasmon resonance sensing devices based on surface plasmon resonance effects have been employed by the industry to detect the species and the concentrations of the targeted biomolecules. The surface plasmon resonance sensing device possesses the following advantages: a. minimal time is required for detection; b. the sample is label-free during the detection process; c. minimal amount of the sample is required; d. detecting the interactions between the sample and the ligands thereof in real-time; and, e. high detection sensitivity.

Figure 1:
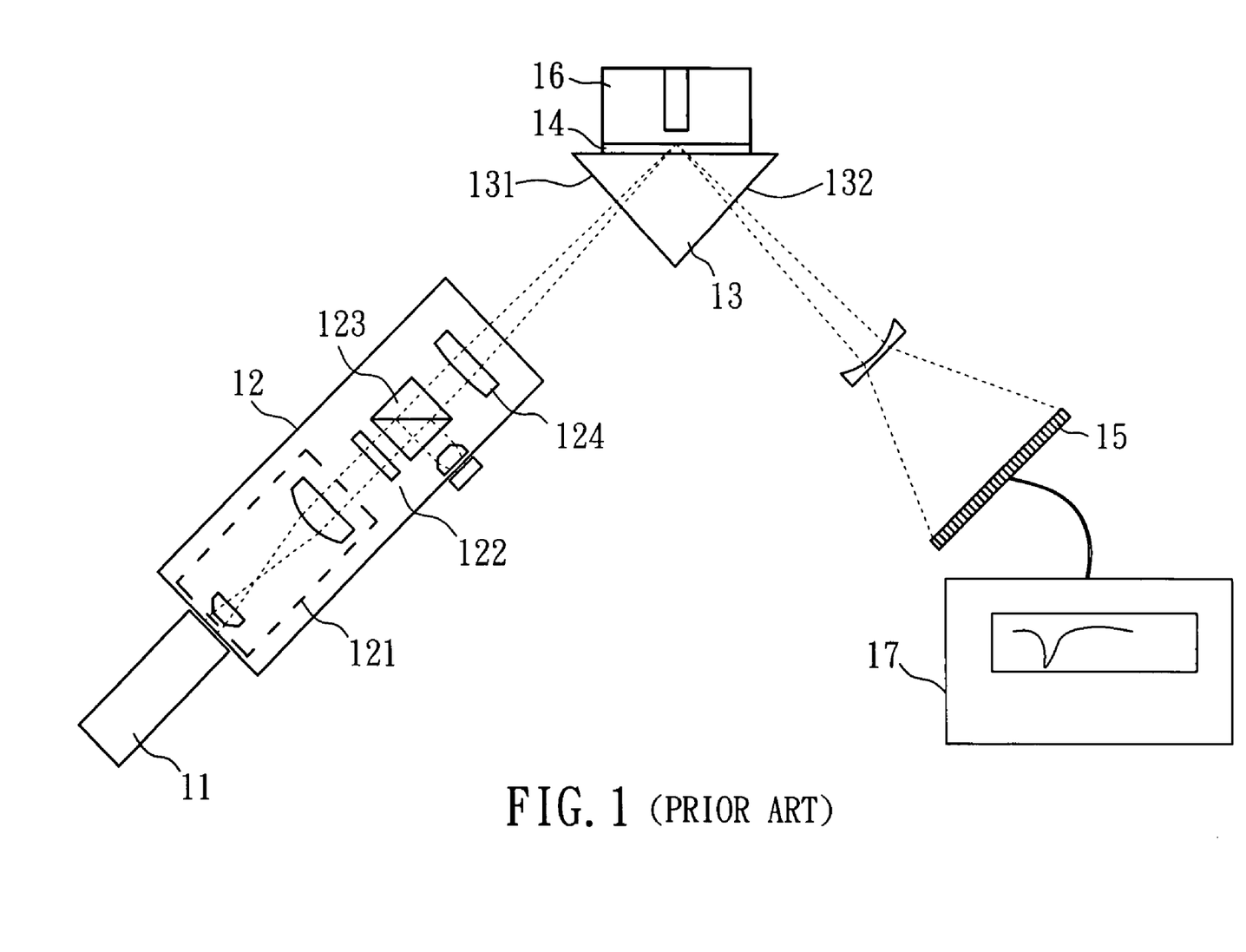
FIG. 1 is a schematic illustration of the conventional surface plasmon resonance sensing device.

FIG. 1 is a schematic illustration of the conventional surface plasmon resonance sensing device, including an incident light source 11, an incident light treatment unit 12, a prism 13, a metal layer 14, an optical detector 15, a detecting target loading unit 16 and a spectrometer 17, wherein the incident light source 11 is a laser diode, and the incident light treatment unit 12 further comprising a beam amplifier 121, a polarizer 122, a spectroscope 123 and a focus lens 124. Therefore, after light generated by the incident light source 11 passes through the incident light treatment unit 12, it has certain frequency, mode and polarization, which is suitable to be used in the detection process. Besides, the metal layer 14 is formed on the back surface of prism 13 by depositing gold or silver particles, either by vapor deposition or sputtering. In the course of detection, the light generated by the incident light source 11 first passes through the incident light treatment unit 12 and then enters a first side 131 of the prism 13. The light is reflected by the metal layer 14, then is emitted from a second side 132 of prism 13, and enters the optical detector 15. Finally, the optical signals received by the optical detector 15 are correspondingly converted to electrical signals, which are provided to spectrometer 17 for analysis of the spectrum profiles thereof.

However, the size of this kind of surface plasmon resonance sensing device is huge, and the locations of the components relative to each other must be maintained accurately, or the light emitting from the incidence light treatment unit will not be correctly reflected by the metal layer formed on the back surface of the prism, and the light will not reach the optical detector. Therefore, the conventional surface plasmon resonance sensing devices have low tolerance to vibrations and are easily damaged by collision, rendering them inappropriate for bringing to the impacted sites by the responding staff.

Furthermore, since the resonant wavelength of the fiber sensing unit of the conventional surface plasmon resonance sensing device is far away from the transmission range of a single-mode fiber or the transmission range of a multi-mode fiber, the surface plasmon resonance signal cannot be transmitted effectively from the fiber sensing unit to the single-mode fiber (or the multi-mode fiber) connected therewith, resulting in signals being lost to a certain level. As a result, the efficiency and the accuracy of the detection of the conventional surface plasmon resonance sensing device are impaired.

Therefore, a surface plasmon resonance sensing device that is portable, easy to operate, having a fiber sensing unit whose resonant wavelength being within the transmission range of a single-mode fiber or the transmission range of a multi-mode fiber, and capable of allowing the responding staff to bring the same to the impacted sites and proceed with accurate detection, is thus required.

SUMMARY OF THE INVENTION

A surface plasmon resonance sensing device, comprising: a light source unit, for providing a light source; a fiber sensing unit including a trench, a cladding layer, a core layer, a first metallic layer and a plurality of dielectric thin film layers, wherein the core layer is surrounded by the cladding layer, and the light source passes through the fiber sensing unit for producing a light signal; an optical sensor, for sensing the light signal and transforming the light signal into a corresponding electric signal; a plurality of fibers being connected with the light source unit, the fiber sensing unit, the optical sensor, respectively; and a computing and displaying unit being connected with the optical sensor, for sensing the electric signal and displaying the result of the computation; wherein the first metallic layer covers the trench, and the plurality of dielectric thin film layers forms on the first metallic layer.

Therefore, since the light signal is transmitted among the light source unit, the fiber sensing unit, and the optical sensor through the plurality of fibers in the surface plasmon resonance sensing device of the present invention, rather than being transmitted in the atmosphere, the surface plasmon resonance sensing device of the present invention can tolerate collision up to a certain level, without the possible of deteriorating the stability of the light path thereof. Besides, as the whole size of the surface plasmon resonance sensing device of the present invention can be further minimized, the portability thereof can be further increased. Moreover, since the plurality of dielectric thin film layers is formed on the surface of the first metallic layer in the fiber sensing unit, the resonant wavelength of the fiber sensing unit of the surface plasmon resonance sensing device of the present invention can be modulated to be within the transmission range of a single-mode fiber or the transmission range of a multi-mode fiber, by means of modulating the film-layer design of the plurality of dielectric thin film layers. As a result, the signal loss caused by the difference between the resonant wavelength of the fiber sensing unit of the surface plasmon resonance sensing device of the present invention and the transmission range of a single-mode fiber, or the transmission range of a multi-mode fiber, can be minimized.

The light source unit used in the surface plasmon resonance sensing device of the present invention can be any kind of conventional light source unit, preferably a laser diode or an LED. The surface plasmon resonance sensing device of the present invention can have any kind of optical detector, preferably a photodiode sensor or a CCD detector. The trench of the fiber sensing unit of the surface plasmon resonance sensing device of the present invention can be manufactured by any conventional process, preferably by a side-polishing process or an etching process. The fiber sensing unit of the surface plasmon resonance sensing device of the present invention can have any number of dielectric thin film layers, preferably from 3 to 5 layers of dielectric thin film layers. The resonant wavelength of the fiber sensing unit of the surface plasmon resonance sensing device of the present invention can have any value, preferably between 840 nm and 860 nm, or between 1300 nm and 1320 nm. The surface plasmon resonance sensing device of the present invention can further include any kind of temperature detector, preferably an electric dipole thermometer. The surface plasmon resonance sensing device of the present invention can further include any kind of temperature controller, preferably a resistance heater or a TE cooler. The fiber of the surface plasmon resonance sensing device of the present invention can be any kind of fiber, preferably a single-mode fiber or a multi-mode fiber. The surface plasmon resonance sensing device of the present invention can further include a plurality of fiber connectors of any kind for connecting the fibers with the fiber sensing unit, preferably FC type fiber connectors, ST fiber connectors, or LC fiber connectors. The surface plasmon resonance sensing device of the present invention can include any kind of power supply unit, preferably a battery set or a plug.

Other objects, advantages, and novel features of the invention will become more apparent from the following detailed description when taken in conjunction with the accompanying drawings.

DETAILED DESCRIPTION OF THE PREFERRED EMBODIMENT

Figure 2A:
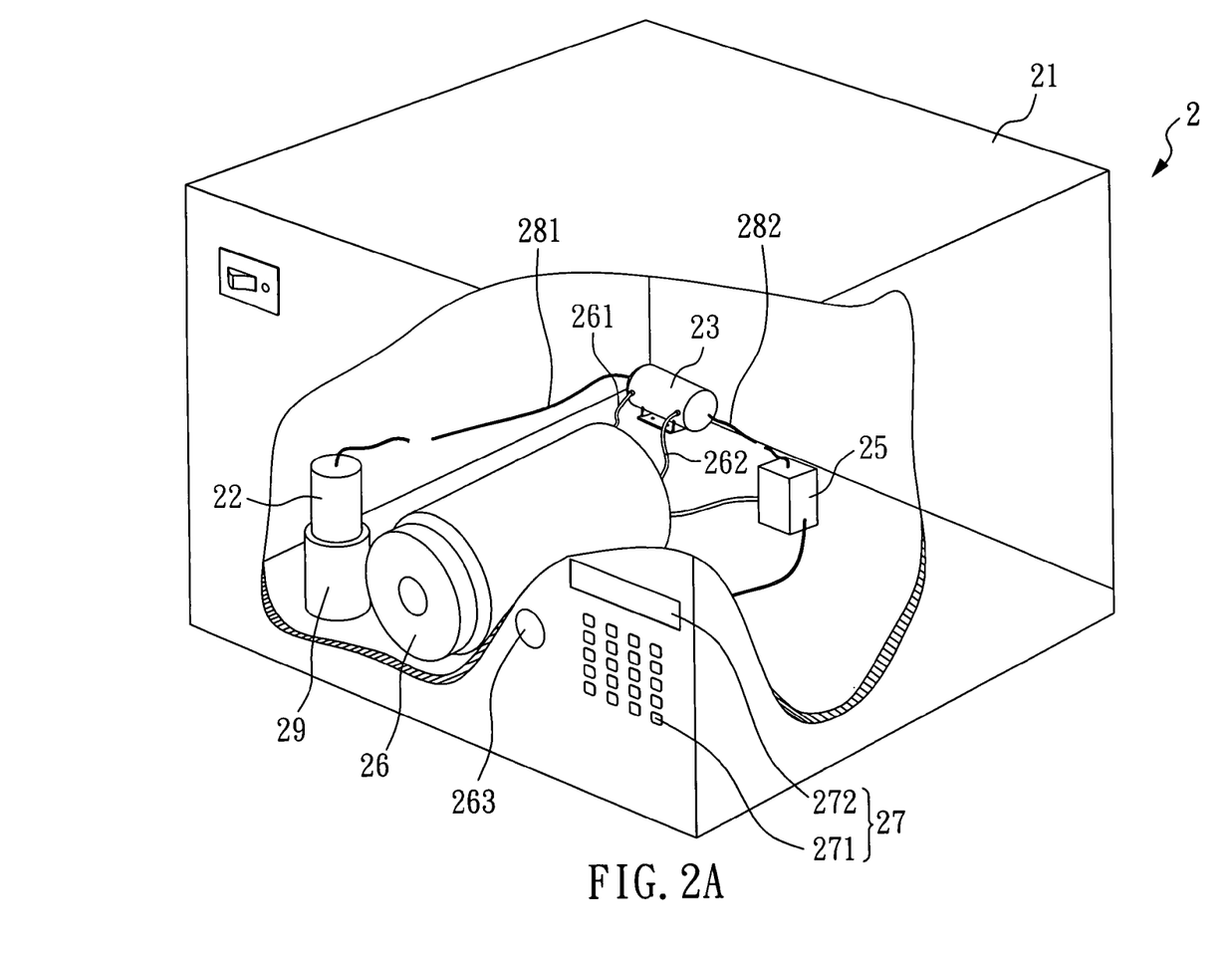
FIG. 2A is a perspective view of the surface plasmon resonance sensing device according to one embodiment of the present invention.
Figure 2B:
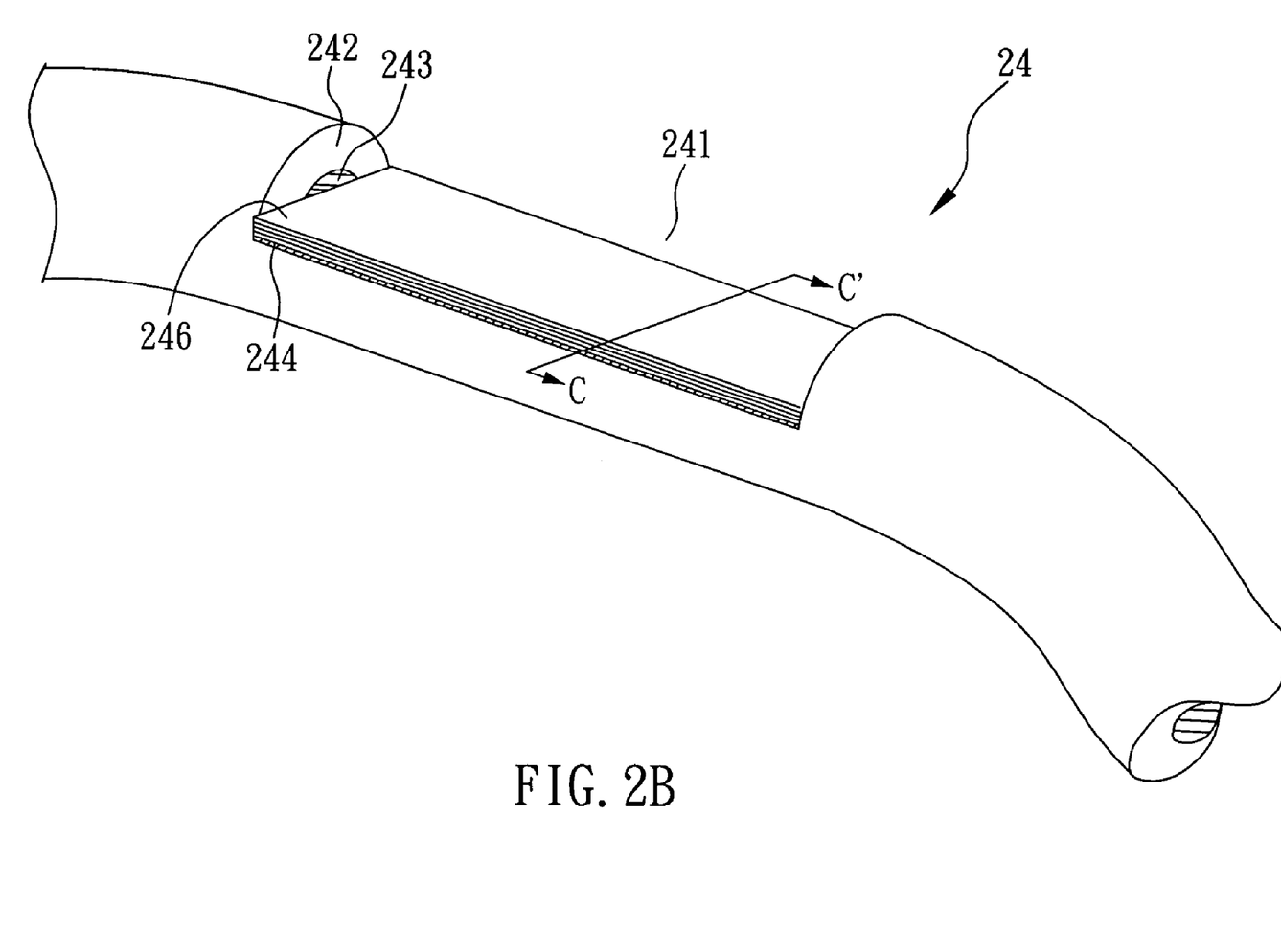
FIG. 2B is a perspective view of the fiber sensing unit of the surface plasmon resonance sensing device according to one embodiment of the present invention.
Figure 2C:
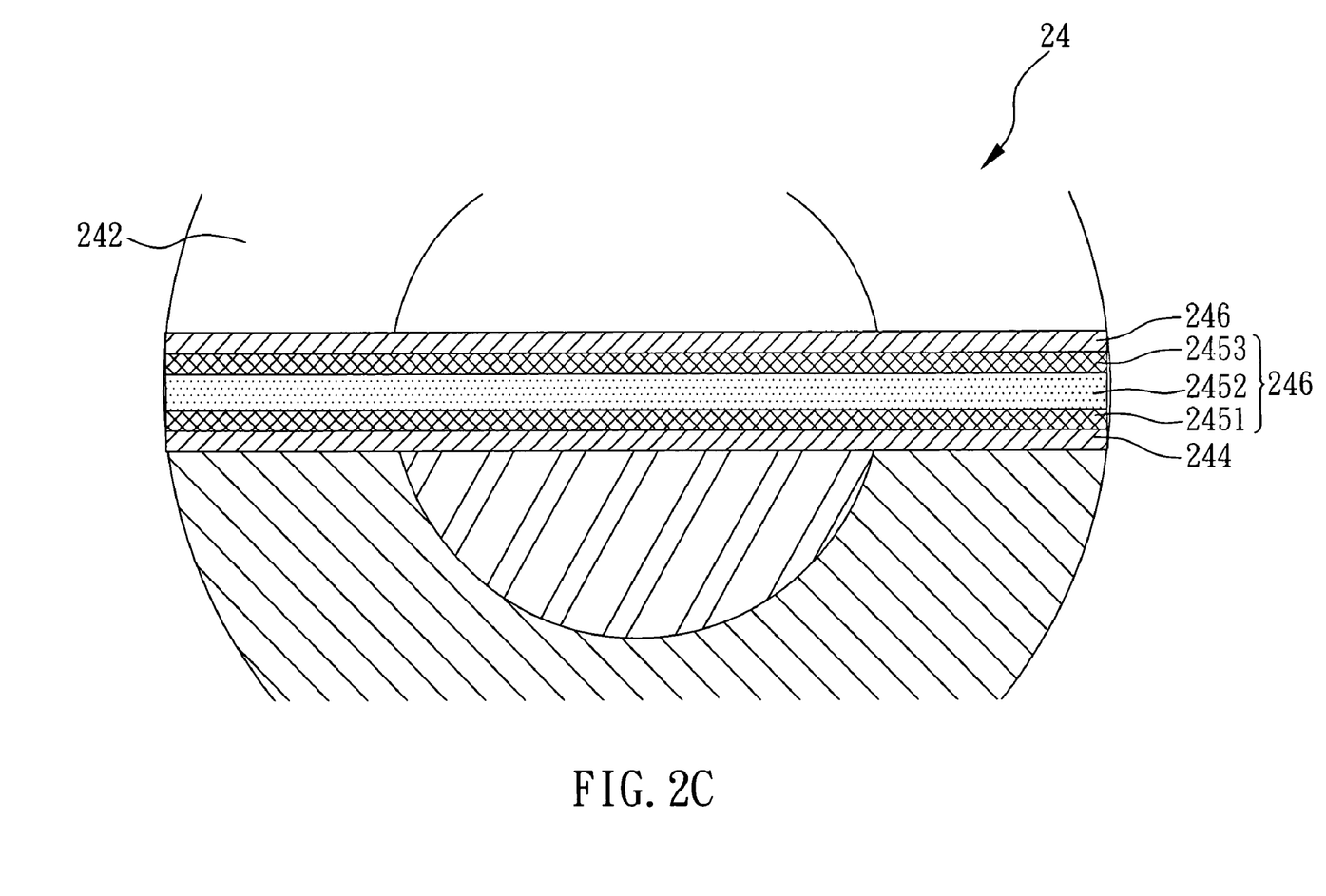
FIG. 2C is a cross-sectional view of the fiber sensing unit of the surface plasmon resonance sensing device according to one embodiment of the present invention, taken along the CC' line of FIG. 2B.

With reference to FIGS. 2A, 2B and 2C, wherein FIG. 2A is a perspective view of the surface plasmon resonance sensing device according to one embodiment of the present invention, FIG. 2B is a perspective view of the fiber sensing unit of the surface plasmon resonance sensing device according to one embodiment of the present invention, and FIG. 2C is a cross-sectional view of the fiber sensing unit of the surface plasmon resonance sensing device according to one embodiment of the present invention, taken along the CC' line of FIG. 2B. As shown in FIGS. 2A and 2B, the surface plasmon resonance sensing device 2 according to one embodiment of the present invention comprises: an outer casing 21, a light source unit 22, a sample tank 23, a fiber sensing unit 24, an optical sensor 25, a solution tank 26, a computing and displaying unit 27, a plurality of fibers 281, 282, and a power unit 29, wherein the fiber sensing unit 24 is in the sample tank 23 and includes a trench 241, a cladding layer 242, a core layer 243, a first metallic layer 244, a plurality of dielectric thin film layers 245, and a second metallic layer 246.

As shown in FIG. 2B, the core layer 243 is surrounded by the cladding layer 242. The first metallic layer 244 covers the trench 241, and the plurality of dielectric thin film layers 245 forms on the first metallic layer 244. Besides, as shown in FIG. 2C, the plurality of dielectric thin film layers 245 includes 3 layers of dielectric thin film layers, i.e. the first silicon dioxide thin film layer 2451, a titanium dioxide thin film layer 2452 on the first silicon dioxide thin film layer 2451, and a second silicon dioxide thin film layer 2453 on the titanium dioxide thin film layer 2452. In the present embodiment, the thickness of the first silicon dioxide thin film layer 2451 is about 30 nm, the thickness of the titanium dioxide thin film layer 2452 is about 60 nm, and the thickness of the second silicon dioxide thin film layer 2453 is about 30 nm. In general, the first metallic layer 244 and the second metallic layer 246 are made of gold or silver.

In the present embodiment, the light source unit 22 is a laser diode, and the light source produced by the light source unit 21 is transmitted to the light source unit 22 in the sample tank 23 via the multi-mode fiber 281. After that, the light signal passing through the fiber sensing unit 24 and carrying the information related to the sample is transmitted to the optical sensor 25 via another multi-mode fiber 282. Later, the optical sensor 25 transforms the light signal into a corresponding electric signal and transmits the electric signal to the computing and displaying unit 27, for further computation purpose.

In the present embodiment, the computing and displaying unit 27 is used to control the operation of the surface plasmon resonance sensing device 2 according to one embodiment of the present invention, and receives the control instructions entered through the button set 271 formed on the surface of the outer casing 21. Besides, the results of calculation by the computing and displaying unit 27 are displayed on the screen 272 formed on the surface of the outer casing 21. The power for operating of the surface plasmon resonance sensing device 2 according to one embodiment of the present invention is provided by a power supply unit 29, which can be a plug with a transformer or a battery set (applied to the occasions where commercial power supply is not available, such as outdoors detecting application).

In addition, the solution tank 26 is loaded with a solution that can provide a suitable environment for the detection, the solution flows in and out through duct 261 and duct 262, respectively, such that the sample tank 23 is maintained in a stable state (e.g., at a state with a certain temperature, pH value, refraction index, etc). The solution generally comprises a buffer, such as physiological saline or deionized water. The solution can be introduced into the solution tank 26 through the opening 263. Furthermore, the solution tank 26 further comprises a manifold valve (not shown), in order to control the flow of the solution.

As shown in FIG. 2B, the fiber sensing unit 24 of the surface plasmon resonance sensing device according to one embodiment of the present invention is formed by executing a side-polishing process on a multi-module fiber, for providing a trench 241 (5 mm long and 62.5

μm deep) thereto. The depth of the trench is greater than the thickness of the cladding layer 242 of the multi-module fiber, rendering the core layer 243 of the multi-module fiber exposed. It is worth noting that neither the length nor the depth of the trench 241 is limited, both of them can be adjusted according to the species of the samples and the environment of the detection (e.g., the refraction index of the solution).

Besides, a first metallic layer 244 (with a depth about 40 nm) is deposited on the surface of the trench 241 by a DC sputtering process or the like. Then, for modulating the resonant wavelength of the fiber sensing unit 24 of the surface plasmon resonance sensing device according to one embodiment of the present invention to be within the transmission range of a single-mode fiber (i.e. between 840 nm and 860 nm) or the transmission range of a multi-mode fiber (i.e. between 1300 nm and 1320 nm), a plurality of dielectric thin film layer 245 is further formed on the surface of the first metallic layer 244 by the DC sputtering process or the like again. It is worth noting that, although the plurality of dielectric thin film layers 245 comprises 3 dielectric thin film layers (i.e. the first silicon dioxide thin film layer 2451, the titanium dioxide thin film layer 2452, and the second silicon dioxide thin film layer 2453), the number of the plurality of dielectric thin film layers is not thus limited. That is, in other applications, the plurality of dielectric thin film layers 245 can comprise a different number of dielectric thin film layers, and can be formed by stacking dielectric thin film layers made of different kinds of material.

Finally, for improving the strength of the surface plasmon resonance effect and the stability of the bonding between the sample and the fiber sensing unit, a second metallic layer 246 can be formed on the surface of the plurality of dielectric thin film layers 245 of the fiber sensing unit 24, by the DC sputtering process or the like.

The detection procedures of the surface plasmon resonance sensing device according to one embodiment of the present invention are described with reference to FIG. 2A to FIG. 2C as follows:

First, the fiber sensing unit 24 having a sample thereon is loaded in sample tank 23, and is connected with the multi-module fibers 281 and 282 through the optical-fiber connectors (not shown). Then, the light source generated by the light source unit 22 passes through the fiber sensing unit 24 in the sample tank 23 and reaches the optical sensor 25.

Subsequently, the pump (not shown) is switched on, and the solution continuously flows in and out of sample tank 23 through the duct 261 and the duct 262, forming a circulation system. In addition, the solution tank 26 further comprises an electric dipole thermometer (not shown) and a TE cooler therein, in order to measure and maintain the temperature of the solution, respectively. When the temperature of the solution is stable, the light source unit 22 is activated by the computing and displaying unit 27 and the light source unit 22 provides a light source having a certain frequency in a range and intensity, which then reaches the fiber sensing unit 24 in sample tank 23 through the multi-module fiber 281.

At that moment, a surface plasmon resonance effect is generated due to the presence of the sample on the surface of the second metallic layer 246 of the fiber sensing unit 24, that is, after passing through the fiber sensing unit 24, the spectrum distribution of the light changes accordingly with the variations of the sample in species, concentrations, and the action forces between the sample and the second metallic layer 246.

As mentioned, the spectrum distribution changes after the light has passed through the fiber sensing unit 24, and then the light reaches the optical sensor 25 through the multi-module fiber 282. The optical signals are then correspondingly converted to electric signals by the optical sensor 25, then the electric signals are provided to the computing and displaying unit 27 connected therewith. After proper procedures have been executed in the computing and displaying unit 27, a spectrum distribution chart is displayed on the screen 272. Alternatively, the species and concentrations of the sample can be displayed directly on screen 272, after comparing thereof to database stored in the memory of the computing and displaying unit 27.

Figure 3:
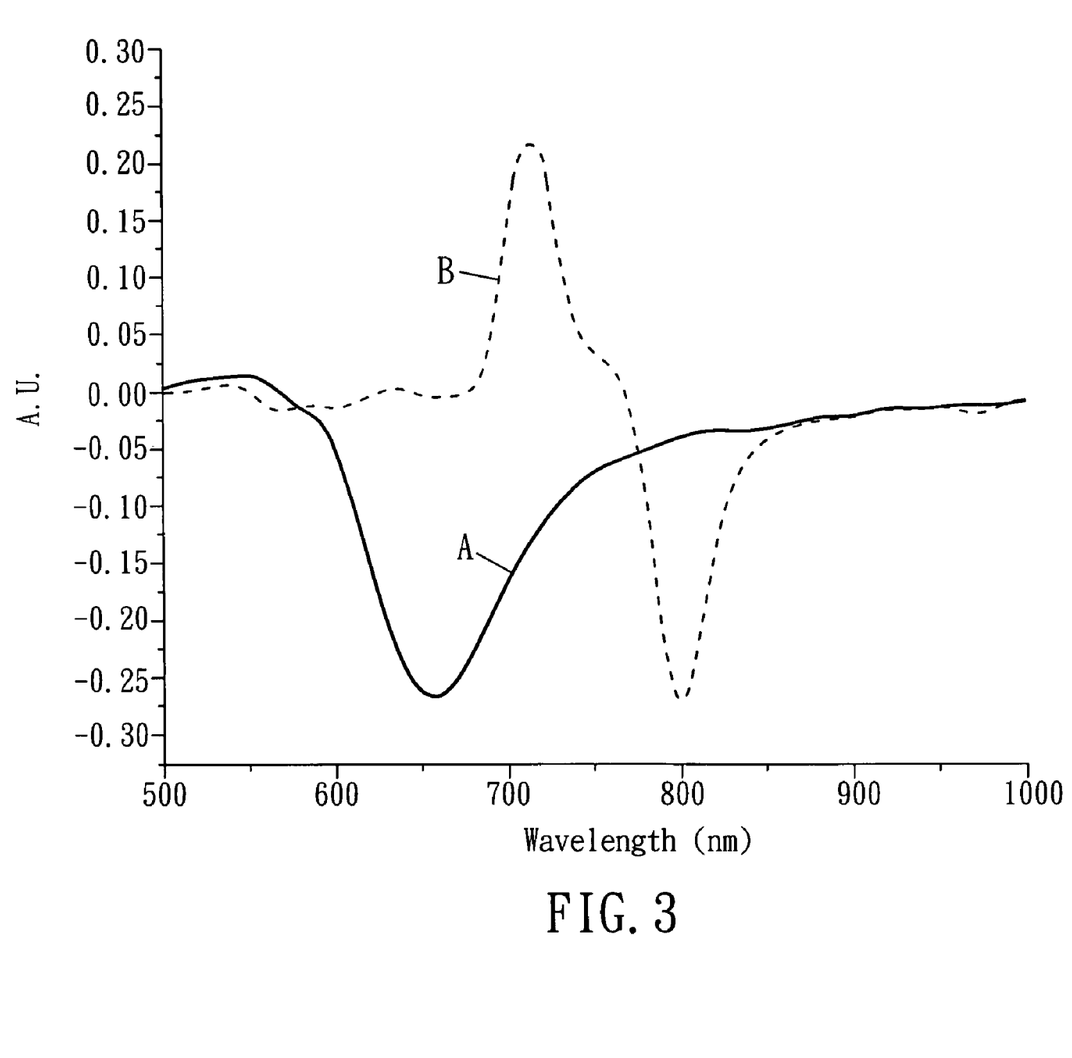
FIG. 3 displays the surface plasmon resonance spectrums of a sample detected by a fiber sensing unit without any dielectric thin film layer thereon, and by the fiber sensing unit of the surface plasmon resonance sensing device according to one embodiment of the present invention.

FIG. 3 displays the surface plasmon resonance spectrums of a sample detected by a fiber sensing unit without any dielectric thin film layer thereon, and by the fiber sensing unit of the surface plasmon resonance sensing device according to one embodiment of the present invention. In the figure, a curve A represents the surface plasmon resonance spectrum of the sample detected by the fiber sensing unit without any dielectric thin film layer thereon, while a curve B represents the surface plasmon resonance spectrum of the sample detected by the fiber sensing unit of the surface plasmon resonance sensing device according to one embodiment of the present invention. It is worth noting that the only difference between the above-mentioned two kinds of fiber sensing unit is the existence of the plurality of dielectric thin film layers.

As shown in FIG. 3, the resonant wavelength of the surface plasmon resonance spectrum represented by the curve A is between 650 nm and 670 nm. The resonant wavelength of the surface plasmon resonance spectrum represented by the curve B is between 800 nm and 820 nm. Besides, the transmission range of a multi-mode fiber is generally between 840 nm and 860 nm. Therefore, compared with the resonant wavelength of the surface plasmon resonance spectrum detected by the fiber sensing unit without any dielectric thin film layer thereon, the resonant wavelength of the surface plasmon resonance spectrum detected by the fiber sensing unit of the surface plasmon resonance sensing device according to one embodiment of the present invention is much closer to the transmission range of a multi-mode fiber. In other words, by modulating the film-layer design of the plurality of dielectric thin film layers of the fiber sensing unit, such as changing the film thickness of each layer of the plurality of dielectric thin film layers or the number of layers of the plurality of dielectric thin film layers, the resonant wavelength of the fiber sensing unit of the surface plasmon resonance sensing device according to one embodiment of the present invention can be shifted to be within the transmission range of a multi-mode fiber.

Figure 4:
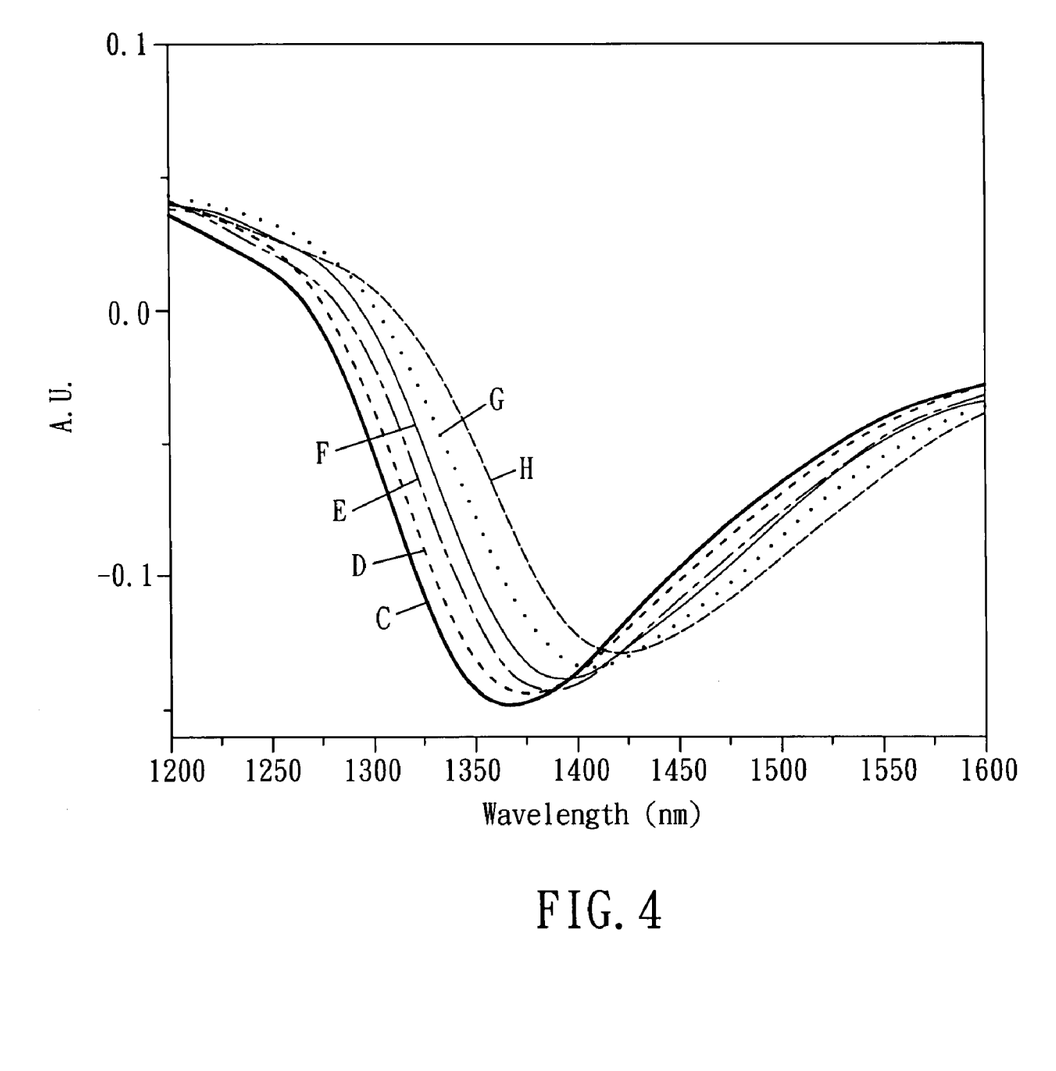
FIG. 4 displays the detection result of 6 kinds of glucose solution with different concentration, detected by the surface plasmon resonance sensing device according to one embodiment of the present invention.

FIG. 4 displays the detection result of 6 kinds of glucose solution with different concentration, detected by the surface plasmon resonance sensing device according to one embodiment of the present invention. In the figure, a curve C represents the detection result of deionized water. A curve D represents the detection result of a glucose solution with 2% concentration. A curve E represents the detection result of a glucose solution with 4% concentration. A curve F represents the detection result of a glucose solution with 6% concentration. A curve G represents the detection result of a glucose solution with 8% concentration. A curve H represents the detection result of a glucose solution with 10% concentration. As shown in FIG. 4, regardless of the concentration of the glucose solution to be detected, the resonant wavelength of the fiber sensing unit of the surface plasmon resonance sensing device of the present invention is close, or even within the transmission range of a single-mode fiber (i.e. between 1300 nm and 1320 nm). Besides, as each of the curves can be easily identified in FIG. 4, the surface plasmon resonance sensing device according to one embodiment of the present invention has a certain level of ability for identifying the difference in concentration of a glucose solution.

In conclusion, since the light signal is transmitted among the light source unit, the fiber sensing unit, and the optical sensor through the plurality of fibers in the surface plasmon resonance sensing device of the present invention, rather than being transmitted in the atmosphere, the surface plasmon resonance sensing device of the present invention can tolerate collision up to a certain level, without the possible of deteriorating the stability of the light path thereof. Besides, as the whole size of the surface plasmon resonance sensing device of the present invention can be further minimized, the portability thereof can be further increased. Moreover, since the plurality of dielectric thin film layers is formed on the surface of the first metallic layer in the fiber sensing unit, the resonant wavelength of the fiber sensing unit of the surface plasmon resonance sensing device of the present invention can be modulated to be within the transmission range of a single-mode fiber or the transmission range of a multi-mode fiber, by means of modulating the film-layer design of the plurality of dielectric thin film layers. As a result, the signal loss caused by the difference between the resonant wavelength of the fiber sensing unit of the surface plasmon resonance sensing device of the present invention and the transmission range of a single-mode fiber, or the transmission range of a multi-mode fiber, can be minimized.

Although the present invention has been explained in relation to its preferred embodiment, it is to be understood that many other possible modifications and variations can be made without departing from the scope of the invention as hereinafter claimed.

What is claimed is:

1. A surface plasmon resonance sensing device, comprising:
   a light source unit, for providing a light source;
   a fiber sensing unit including a trench, a cladding layer, a core layer, a first metallic layer, a second metallic layer and a plurality of dielectric thin film layers, wherein the core layer is surrounded by the cladding layer, and the light source passes through the fiber sensing unit for producing a light signal;
   an optical sensor, for sensing the light signal and transforming the light signal into a corresponding electric signal;
   a plurality of fibers being connected with the light source unit, the fiber sensing unit, the optical sensor, respectively; and
   a computing and displaying unit being connected with the optical sensor, for sensing the electric signal and displaying the result of the computation;
   wherein the first metallic layer covers the trench, the plurality of dielectric thin film layers forms on the first metallic layer; and the second metallic layer forms on the plurality of dielectric thin film layers.

2. The surface plasmon resonance sensing device as claimed in claim 1, further comprises a sample tank, for storing the fiber sensing unit and a solution including a buffer therein.

3. The surface plasmon resonance sensing device as claimed in claim 1, wherein the light source unit is a laser diode, and the optical sensor is a photodiode sensor.

4. The surface plasmon resonance sensing device as claimed in claim 1, wherein the plurality of dielectric thin film layers includes at least three layers of dielectric thin film layers.

5. The surface plasmon resonance sensing device as claimed in claim 1, wherein the plurality of dielectric thin film layers includes a first silicon dioxide thin film layer, a titanium dioxide thin film layer on the first silicon dioxide thin film layer, and a second silicon dioxide thin film layer on the titanium dioxide thin film layer.

6. The surface plasmon resonance sensing device as claimed in claim 1, wherein the first metallic layer and the second metallic layer are made of gold or silver.

7. The surface plasmon resonance sensing device as claimed in claim 1, wherein the trench is manufactured by a side-polished process executed on a fiber.

8. The surface plasmon resonance sensing device as claimed in claim 1, wherein the plurality of fibers is a single-mode fiber or a multi-mode fiber.

9. The surface plasmon resonance sensing device as claimed in claim 1, wherein the resonant wavelength of the fiber sensing unit is between 840 nm and 860 nm, or between 1300 nm and 1320 nm.

10. A surface plasmon resonance sensing device, comprising:
    a light source unit, for providing a light source;
    a fiber sensing unit including a a multi-module fiber including a cladding layer and a core layer, said fiber having a trench therein having a flat bottom surface at a depth within the trench exceeding the thickness of the cladding layer and exposing a portion of the core layer;
    said flat bottom surface having a first metallic layer, a second metallic layer and a plurality of dielectric thin film layers, wherein the core layer is surrounded by the cladding layer, and the light source passes through the fiber sensing unit for producing a light signal;
    an optical sensor, for sensing the light signal and transforming the light signal into a corresponding electric signal;
    a plurality of fibers being connected with the light source unit, the fiber sensing unit, the optical sensor, respectively; and
    a computing and displaying unit being connected with the optical sensor, for sensing the electric signal and displaying the result of the computation;
    wherein the first metallic layer covers the trench, the plurality of dielectric thin film layers forms on the first metallic layer; and the second metallic layer forms on the plurality of dielectric thin film layers.

11. The surface plasmon resonance sensing device as claimed in claim 10, further comprises a sample tank, for storing the fiber sensing unit and a solution including a buffer therein.

12. The surface plasmon resonance sensing device as claimed in claim 10, wherein the light source unit is a laser diode, and the optical sensor is a photodiode sensor.

13. The surface plasmon resonance sensing device as claimed in claim 10, wherein the plurality of dielectric thin film layers includes at least three layers of dielectric thin film layers.

14. The surface plasmon resonance sensing device as claimed in claim 10, wherein the plurality of dielectric thin film layers includes a first silicon dioxide thin film layer, a titanium dioxide thin film layer on the first silicon dioxide thin film layer, and a second silicon dioxide thin film layer on the titanium dioxide thin film layer.

15. The surface plasmon resonance sensing device as claimed in claim 10, wherein the plurality of dielectric thin film layers includes a first silicon dioxide thin film layer, a titanium dioxide thin film layer on the first silicon dioxide thin film layer, and a second silicon dioxide thin film layer on the titanium dioxide thin film layer, and the trench has a length of 5 mm and a depth of 62.5 microns.

16. The surface plasmon resonance sensing device as claimed in claim 15, wherein the first metallic layer and the second metallic layer are made of gold or silver.

17. The surface plasmon resonance sensing device as claimed in claim 10, wherein the trench is manufactured by a side-polished process executed on a fiber.

18. The surface plasmon resonance sensing device as claimed in claim 10, wherein the plurality of fibers is a single-mode fiber or a multi-mode fiber.

19. The surface plasmon resonance sensing device as claimed in claim 10, wherein the resonant wavelength of the fiber sensing unit is between 840 nm and 860 nm, or between 1300 nm and 1320 nm.

\* \* \* \* \*